United States Patent
Chandar et al.

(10) Patent No.: US 10,144,908 B2
(45) Date of Patent: *Dec. 4, 2018

(54) LIQUID SOAP HAVING ENHANCED ANTIBACTERIAL ACTIVITY

(71) Applicant: Conopco, Inc., Englewood Cliffs, NJ (US)

(72) Inventors: Prem Chandar, Closter, NJ (US); Guohui Wu, Woodbridge, CT (US); Nitish Kumar, Bihar (IN); Vamsi Krishna Manthena, Chattishgarh (IN); Vibhav Ramrao Sanzgiri, Mumbai (IN); Anat Shiloach, Trumbull, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 151 days.

This patent is subject to a terminal disclaimer.

(21) Appl. No.: 14/784,178

(22) PCT Filed: Apr. 9, 2014

(86) PCT No.: PCT/EP2014/057189
§ 371 (c)(1),
(2) Date: Oct. 13, 2015

(87) PCT Pub. No.: WO2014/170186
PCT Pub. Date: Oct. 23, 2014

(65) Prior Publication Data
US 2016/0053206 A1  Feb. 25, 2016

(30) Foreign Application Priority Data

Apr. 16, 2013 (IN) .......................... 1429/MUM/2013

(51) Int. Cl.
| | |
|---|---|
| *C11D 9/10* | (2006.01) |
| *C11D 3/48* | (2006.01) |
| *C11D 9/00* | (2006.01) |
| *C11D 9/26* | (2006.01) |
| *C11D 17/08* | (2006.01) |

(52) U.S. Cl.
CPC .................. *C11D 9/10* (2013.01); *C11D 3/48* (2013.01); *C11D 9/00* (2013.01); *C11D 9/26* (2013.01); *C11D 17/08* (2013.01)

(58) Field of Classification Search
CPC .... C11D 3/48; C11D 9/00; C11D 9/10; C11D 9/18; C11D 9/26; C11D 11/0005; C11D 11/0011; C11D 11/0058; C11D 17/08; A61Q 19/10; A61K 8/19
See application file for complete search history.

(56) References Cited

U.S. PATENT DOCUMENTS

| | | | |
|---|---|---|---|
| 2,864,769 A | 12/1958 | Lutz et al. | |
| 3,050,467 A | 8/1962 | Horowtiz et al. | |
| 3,408,299 A * | 10/1968 | Henry | ....................... C11D 9/20 510/396 |
| 4,861,489 A * | 8/1989 | Swift | ........................ C02F 1/42 210/167.3 |
| 6,294,186 B1 | 9/2001 | Beerse et al. | |
| 6,794,344 B2 | 9/2004 | Taylor et al. | |
| 2006/0115440 A1 | 6/2006 | Arata | |
| 2008/0045491 A1 | 2/2008 | Fitchmun | |
| 2010/0098776 A1 | 4/2010 | Carnali et al. | |
| 2011/0223114 A1 | 9/2011 | Chakrabortty et al. | |
| 2011/0224120 A1 | 9/2011 | Meine et al. | |
| 2012/0034314 A1 | 2/2012 | Levison et al. | |
| 2012/0201902 A1* | 8/2012 | Modak | ................... A01N 31/02 424/618 |

FOREIGN PATENT DOCUMENTS

| | | |
|---|---|---|
| CA | 586350 | 11/1959 |
| CN | 101659911 | 3/2010 |
| CN | 102186341 | 9/2011 |
| GB | 759950 | 10/1956 |
| GB | 847257 | 9/1960 |
| GB | 887247 | 1/1962 |
| JP | 9003492 | 1/1997 |
| KR | 20000020781 | 4/2000 |
| KR | 20010069644 | 7/2001 |
| WO | WO9723594 | 7/1997 |
| WO | WO9840465 | 9/1998 |
| WO | WO2011131422 | 10/2011 |

OTHER PUBLICATIONS

Feng et al. A Machanicstic study of the antibacterial effect of silver ions on *Escherichia coil* and *Staphyococcus aureus*. Journal of Biomedical Material Research. vol. 52, issue 4, Oct. 2000.*
Keeping Hands Clean. Center for Disease Control and Prevention (CDC), Feb. 1, 2011.*
Soap, Wikipedia, previous version from Apr. 5, 2012.*
Search Report in PCTEP2014057189, dated Jun. 6, 2014.
Written Opinion in PCTEP2014057189, dated Jun. 6, 2014.
IPRP1 in PCTEP2014057189, dated Jul. 10, 2015.
IPRP1 in PCTEP2014057190, dated Jul. 3, 2015.
Search Report in EP13172451, dated Apr. 28, 2014, EP.
Search Report in EP13172455, dated Apr. 28, 2014, EP.
Search Report in PCTEP2014057190, dated Jul. 1, 2014.

(Continued)

*Primary Examiner* — Sharidan Carrillo

(74) *Attorney, Agent, or Firm* — Ronald A. Koatz

(57) ABSTRACT

Method of cleansing human skin employing an aqueous soap composition comprising of fatty acid soap, at least one silver (I) compound having a silver ion solubility (in water at 25° C.) of at least $1 \times 10^{-4}$ mol/L, and water, which composition provides biocidal activity against Gram positive bacteria in particular *S. aureus*, in relatively short contact periods.

3 Claims, No Drawings

(56) References Cited

OTHER PUBLICATIONS

Written Opinion 1 in PCTEP2014057190, dated Jul. 1, 2014.
Written Opinion 2 in PCTEP2014057189, dated Mar. 18, 2015.
Written Opinion 2 in PCTEP2014057190, dated Mar. 18, 2015.
Written Opinion in EP13172451, dated Apr. 28, 2014, EP.
Written Opinion in EP13172455, dated Apr. 28, 2014, EP.
Copending application for Chandar et al.; Filed: Oct. 13, 2015 entitled Soap Bar Having Enhanced Antibacterial Activity.

* cited by examiner

LIQUID SOAP HAVING ENHANCED ANTIBACTERIAL ACTIVITY

FIELD OF THE INVENTION

The subject invention relates to soap-based liquid cleansing formulations having enhanced antibacterial activity against Gram positive and Gram negative microorganisms, as well as to methods of enhancing antibacterial activity against Gram positive and Gram negative microorganisms in skin cleaning applications having relatively short contact times.

BACKGROUND OF THE INVENTION

Soap compositions, for example, bars and liquids, are known to have antibacterial benefits largely associated with the removal of organisms from the skin through the cleansing/detergency action of such products. Additionally, such compositions commonly have biocidal action against many Gram negative bacteria. The biocidal action of soap compositions against Gram positive bacteria, such as, for example, S. aureus is, however, considerably more limited within the contact times typical of product use, generally under 1 minute, and more commonly on the order of 30 seconds or less. Achieving biocidal action against Gram positive bacteria is especially problematic in the case of high pH liquid soap products, i.e. liquid soap compositions having pH of from 8 to 11, more particularly from 9 to 11, at 25° C.

Various routes to improving the biocidal activity of soap compositions has been suggested. For example, U.S. Pat. No. 6,794,344 (Taylor et al.) discloses soap bars that comprise at least about 50% soap having alkyl chain lengths of 8-10 carbon atoms, about 10% to about 30% hydric solvent, and free acid, preferably free fatty acid, such that the pH of a 10% aqueous solution of the soap bar is no greater than about 9. The soap bar is therein characterized as exhibiting, in the test therein described, a log reduction against Gram positive bacteria of at least 3 after 30 seconds of contact at 40° C., as measured against S. aureus. Information presented in Table 3 of Taylor et al. compares the effect of free fatty acid content as function of pH on antibacterial activity against S. aureus.

Routes to achieving an antimicrobial benefit in cleansing compositions, including soap-based compositions, as well as compositions based on synthetic anionic surfactant, i.e., "syndet", also include the use of one or more agents having a biocidal effect.

U.S. Patent Application Publication No. 2012/003413 (Levison et al.) discloses antiseptic formulations therein said to be capable of providing antimicrobial properties over an extended period of time. The formulations therein disclosed include chelated metal ions (including chelated silver ions) and a fixative polymer having the capacity to bond the chelated metal ions to the skin. In Table IV thereof, Levinson et al. provides the formulation for a liquid soap based on synthetic anionic surfactant. The formulation includes, among other ingredients, sodium laureth sulfate, sodium lauryl sulphate, propylene glycol, cocamidopropyl betaine, cocamide DEA, ethyol alcohol, macadamia glycerides, acrylate cross polymer, silver dihydrogen citrate, and tetrasodium EDTA.

WO 01/1131422 discloses toilet soap therein characterized as having antimicrobic properties, which soap contains what is therein termed a "soap basis", functional additives, and bentonite powder intercalated with $Ag^+$ and/or $Cu^{2+}$ ions.

U.S. Patent Application Publication No. 2010/0098776 (Carnali et al.) discloses soap-based liquid wash formulations therein said to have enhanced antibacterial activity, which compositions include from 0.01 to 10 wt. % antimicrobial agent, e.g., silver particles, zinc particles, copper particles or mixtures thereof. The soap-based formulations are said to include 10 to 50% by weight, preferably 25 to 40% by weight, more preferably 30 to 40% by weight of a fatty acid blend of $C_{12}$-$C_{18}$ fatty acids (the fatty acid blend being further characterized as having degrees of neutralization between 70% and 90%); 10 to 40% by weight of co-solvent such as, for example glycerol, ethylene glycol, propylene glycol, diethylene glycol, dipropylene glycol and mixtures thereof, and less than 18%, preferably less than 16% by weight water, such that the ratio of co-solvent to water lies in the range of 0.4-10, preferably 0.8 to 7, more preferably 1.0 to 5.

U.S. Pat. No. 3,050,467 (Horowitz et al.) discloses antiseptic cleaners, for example soaps and detergents that include a mixture of from about 90% to about 99% by weight of a water-soluble soap and from about 10% to about 1% by weight of a silver salt of partially depolymerized alginic acid. The recited amount of alginic acid is said to provide the compositions with a silver content of from 0.01 to 1% by weight.

U.S. Patent Application Publication No. 2006/0115440 (Arata et al.) discloses personal care products that include silver dihydrogen citrate and a physiologically acceptable medium. The compositions are said to include silver ion at a concentration of 50 ppb to 10,000 ppm, such concentrations being based on the total weight of silver ion per unit volume of the final composition (if liquid) or per unit weight of the final composition (if solid).

There remains a need for personal cleaning methods that provide improved biocidal activity against Gram positive bacteria in the relatively short contact times typical of wash-off cleansing applications, i.e., contact times of less than 1 minute, more particularly 30 seconds or less, even more particularly 10 seconds or less, as well as for liquid soap formulations, in particular high pH liquid soap formulations, suitable for use in such methods.

SUMMARY OF THE INVENTION

It has now been found that the direct biocidal action, i.e., germ kill, of liquid soaps against Gram positive bacteria including, for example, S. aureus, can be enhanced, within the short contact times associated with liquid soap use, through the incorporation therein of selected silver (I) compounds, more particularly silver (I) compounds having a selected silver ion solubility value, as hereinafter more particularly described. Moreover, it has been found that such germ kill may be achieved using the silver (I) compounds at concentrations at which the compounds themselves, in water, at comparable pH (i.e., 8 to 11, more particularly 9 to 11), fail to provide effective biocidal activity within the desired short term contact times typical of liquid soap applications, i.e., contact times of less than 1 minute, more particularly 30 seconds or less, even more particularly 10 seconds or less.

Without wishing to be bound by theory, the subject inventors have found that in the context of soap-based liquid cleansing formulations the role of such low levels of the silver (I) compounds is to modify the environment of the microorganisms so as to enable the soap molecules to act as biocides. Thus, the subject invention is directed, in part, to enhancing the antibacterial activity of soap itself against Gram positive and Gram negative organisms.

Given the relatively high cost of silver, such low levels of silver compound provides for significant cost benefits, compared to the higher levels needed for the silver compounds themselves to have a significant biocidal effect within the contact times of interest. Additionally, the low levels of silver compound are desirable from both a sensory and process vantage.

In one embodiment there is provided a liquid cleansing formulation for personal care applications (the term "liquid cleansing formulation" is herein alternatively referred to as "personal cleansing formulation" or "liquid soap formulation"), the formulation comprising:
 (a) 5 to 65% by weight, based on the total weight of the formulation, of fatty acid soap,
 (b) 0.1 to 100 ppm by weight, preferably from 1 to 50 ppm, more preferably from 5 to 20 ppm, based on the total weight of the formulation, of at least one silver (I) compound having a silver ion solubility (in water at 25° C.) of at least $1 \times 10^{-4}$ mol/L; and
 (c) 20 to 90% by weight water,
 wherein:
 at 25° C., the formulation has a pH in a range of from 8 to 11, more particularly from 9 to 11.

In a further embodiment there is provided a method of enhancing the antibacterial effectiveness against Gram positive bacteria of a high pH liquid cleansing formulation based on fatty acid soap which comprises incorporating into said liquid cleansing formulation from 0.1 to 100 ppm by weight, more particularly from 1 to 50 ppm, even more particularly from 5-20 ppm of at least one silver (I) compound having a silver ion solubility (in water at 25° C.) of at least $1 \times 10^{-4}$ mol/L, wherein the resulting formulation preferably provides a $Log_{10}$ Reduction against S. aureus ATCC 6538 of at least 2.5, preferably at least 3, at a contact time of 30 seconds and even more preferably provides a $Log_{10}$ Reduction against S. aureus ATCC 6538 of at least 1.5, more preferably at least 2, at a contact time of 10 seconds, in the In Vitro-Time-Kill Protocol hereinafter described.

In another embodiment there is provided a method of cleansing human skin, more particularly a method of cleansing human skin that reduces Gram positive bacteria on same, which comprises;
 (i) lathering or otherwise foaming a liquid cleansing formulation comprising:
  (a) from 5 to 65% by weight, based on the total weight of the formulation, of fatty acid soap,
  (b) 0.1 to 100 ppm by weight, more preferably from 1 to 50 ppm, based on the total weight of the formulation, of at least one silver (I) compound having a silver ion solubility (in water at 25° C.) of at least $1 \times 10^{-4}$ mol/L; and
  (c) 20 to 90% by weight water,
 optionally, with additional water,
 (ii) applying the foamed composition to the skin for a contact period of less than 1 minute, more particularly 30 seconds or less, even more particularly 10 seconds or less, and
 (iii) rinsing the foamed composition from the skin.

In yet another embodiment there is provided a method of reducing Gram positive bacteria on human skin which comprises:
 (I) applying to the human skin an aqueous soap composition that includes:
  (a) from 0.2 to 25% by weight of fatty acid soap,
  (b) at least one silver (I) compound having a silver ion solubility (in water at 25° C.) of at least $1 \times 10^{-4}$ mol/L, the aqueous soap composition having been prepared by diluting, as needed, a liquid cleansing formulation comprising:
   (i) from 5 to 65% by weight, based on the total weight of the formulation of fatty acid soap,
   (ii) 0.1 to 100 ppm by weight, more preferably from 1 to 50 ppm, based on the total weight of the formulation, of at least one silver (I) compound having a silver ion solubility (in water at 25° C.) of at least $1 \times 10^{-4}$ mol/L; and
   (iii) 20 to 90% by weight water,
  to said fatty acid content of 0.2 to 25 wt %,
 (II) allowing the aqueous soap composition to remain on the skin for a contact period of under 1 minute, preferably for 30 seconds or less, more preferably for 10 seconds or less, and
 (III) rinsing the aqueous soap composition from the skin.

The liquid cleansing formulation employed in the subject methods commonly has a pH of from 8 to 11, more particularly from 9 to 11. In one or more embodiments the silver content of the liquid cleansing formulation employed in the subject methods is from 5-20 ppm, more particularly from 5 to 15 ppm, based on the total weight of the formulation.

In yet another embodiment of the invention, it has been found that when the liquid cleansing formulations comprising fatty acid soap, silver compounds, and water as noted above (preferably at pH levels noted) are further used in combination with essential oil antimicrobial actives thymol and terpineol, excellent antibacterial effect is obtained. Specifically, combination of salt of silver with both thymol and terpineol have overall antibacterial effect against both Gram positive and Gram negative bacteria.

Each of thymol and terpineol are preferably present at a level of 0.01 to 2% by wt. of the total composition.

Preferably, the thymol and terpineol may be added to the silver-containing compositions of the invention as (a) an antimicrobial composition comprising 0.01 to 2% essential oil active mixture of thymol and terpineol and (b) a hydrotrope (preferably selected from the group consisting of sodium benzoate, sodium toluene sulphonate, sodium cumene sulphonate, sodium xylene sulphonate, sodium salicylate, sodium acetate and mixtures thereof).

Preferably, the silver-containing composition comprises 0.01 to 1% total thymol and terpineol. Additional essential oil actives, e.g., eugenol, geraniol or mixtures, can be used. Another preferred mixture of oils to be used in the silver-containing compositions, for enhanced antibacterial effect, is thymol, terpineol and eugenol.

DETAILED DESCRIPTION OF THE INVENTION

Except in the operating and comparative examples, or where otherwise explicitly indicated, all numbers in this description indicating amounts, parts, percentages, ratios, and proportions of material, physical properties of material, and conditions of reaction are to be understood as modified by the word "about". All parts, percentages, ratios, and proportions of material referred to in this description are by weight unless otherwise indicated.

The term "comprising" is meant not to be limiting to any subsequently stated elements but rather to encompass non-specified elements of major or minor functional importance. In other words, the listed steps, elements or options need not be exhaustive. Whenever the words "including" or "having" are used, these terms are meant to be equivalent to "comprising" as defined above. Where the compositions or formulations of the subject invention are described as "including" or "comprising" specific components or materials, narrower embodiments where the compositions or formulations can "consist essentially of" or "consist of" the recited components or materials are also contemplated.

It should also be noted that in specifying any range of concentration or amount, any particular upper concentration or amount can be associated with any particular lower concentration or amount.

Fatty Acid Soap

The term "fatty acid soap" or, more simply, "soap" is used here in its popular sense, i.e., salts of aliphatic alkane- or alkene monocarboxylic fatty acids preferably having 6 to 22 carbon atoms, and preferably 8 to 18 carbon atoms.

The fatty acid soap should comprise from 5 to 65% by weight, preferably from 10 to 55% by weight of the subject liquid cleansing formulations. The referenced fatty acid levels are for formulations in the form typically provided to consumers, without taking into account dilution in use. In use, formulations containing fatty acid soap at higher levels within such range are typically diluted with water such that the diluted composition that is applied to the skin typically contains 25% or less, more particularly from 0.2 to 25% or less of fatty acid soap.

Typical of the soap salts are alkali metal or alkanol ammonium salts of such fatty acids, although other metal salts thereof, e.g., magnesium salts, may also be employed. Sodium, potassium, magnesium, mono-, di- and tri-ethanol ammonium salts of such acids are among the more common soaps suitable for use herein. In one or more commonly, potassium soaps are used in the formulations of this invention, but up to about 25% of the soap may be sodium or magnesium soaps.

As noted above, the fatty acids from which the soap salts are derived may contain unsaturation. The level of unsaturation should be in accordance with commercially acceptable standards. Excessive unsaturation is normally avoided to minimize color and odor issues. Commonly, not more than to 40 wt. % of the fatty acids from which the soap salts are formed are unsaturated. In one more embodiments, from 10 to 40 wt. %, more particularly from 20 to 40 wt. % of the fatty acids from which the soap salts are formed are unsaturated.

In one or more embodiments it is preferred that the combination of $C_{12}$, $C_{14}$, $C_{16}$, and $C_{18}$ fatty acids accounts for from 90 to 100 wt %, more particularly from 95 to 100 wt. % of the total fatty acids from which the soap salts are formed and, preferably, that the combination of $C_{16}$ and $C_{18}$ fatty acids accounts for from 10 to 35 wt. %, more particularly from 12 to 30 wt %, even more particularly from 14 to 28 wt. %, of the total fatty acids from which the soap salts are formed. Preferably, the total amount of $C_8$ and $C_{10}$ fatty acids is less than 5 wt %, and preferably is less than 3 wt. % of the fatty acids from which the soap salts are formed.

Silver Compounds

The silver compounds employed as in the subject formulations and compositions are one or more water-soluble silver (I) compounds having a silver ion solubility at least $1.0 \times 10^{-4}$ mol/L (in water at 25° C.). Silver ion solubility, as referred to herein, is a value derived from a solubility product (Ksp) in water at 25° C., a well known parameter that is reported in numerous sources. More particularly, silver ion solubility [Ag+], a value given in mol/L may be calculated using the formula:

$$[Ag+] = (Ksp \cdot x)^{(1/(x+1))},$$

wherein Ksp is the solubility product of the compound of interest in water at 25° C., and x represents the number of moles of silver ion per mole of compound. It has been found that silver (I) compounds having a silver ion solubility of at least $1 \times 10^{-4}$ mol/L are suitable for use herein. Silver ion solubility values for a variety of silver compounds are given in Table 1:

TABLE 1

Silver ion Solubility Values

| Silver Compound | X | Ksp (mol/L in water at 25° C.) | Silver Ion Solubility [Ag+] (mol/L in water at 25° C.). |
|---|---|---|---|
| silver nitrate | 1 | 51.6 | 7.2 |
| Silver acetate | 1 | $2.0 \times 10^{-3}$ | $4.5 \times 10^{-2}$ |
| Silver sulfate | 2 | $1.4 \times 10^{-5}$ | $3.0 \times 10^{-2}$ |
| Silver benzoate | 1 | $2.5 \times 10^{-5}$ | $5.0 \times 10^{-3}$ |
| Silver salicylate | 1 | $1.5 \times 10^{-5}$ | $3.9 \times 10^{-3}$ |
| Silver carbonate | 2 | $8.5 \times 10^{-12}$ | $2.6 \times 10^{-4}$ |
| Silver citrate | 3 | $2.5 \times 10^{-16}$ | $1.7 \times 10^{-4}$ |
| Silver oxide | 1 | $2.1 \times 10^{-8}$ | $1.4 \times 10^{-4}$ |
| Silver phosphate | 3 | $8.9 \times 10^{-17}$ | $1.3 \times 10^{-4}$ |
| Silver chloride | 1 | $1.8 \times 10^{-10}$ | $1.3 \times 10^{-5}$ |
| Silver bromide | 1 | $5.3 \times 10^{-13}$ | $7.3 \times 10^{-7}$ |
| Silver iodide | 1 | $8.3 \times 10^{-17}$ | $9.1 \times 10^{-9}$ |
| Silver sulfide | 2 | $8.0 \times 10^{-51}$ | $2.5 \times 10^{-17}$ |

Among the silver (I) compounds suitable for use herein are silver oxide, silver nitrate, silver acetate, silver sulfate, silver benzoate, silver salicylate, silver carbonate, silver citrate and silver phosphate, with silver oxide, silver sulfate and silver citrate being of particular interest in one or more embodiments. In at least one preferred embodiment the silver (I) compound comprises silver oxide.

In at least one embodiment the silver compound is not silver dihydrogen citrate. In another embodiment the silver compound is not a salt of alginic acid or substantially depolymerized alginic acid. In one preferred embodiment the silver compound is not in the form of nano particles, attached to nano particles or part of intercalated silicates such as, for example, bentonite.

In one or more embodiments, the ratio by weight of silver compound to soap salt in the aqueous soap compositions employed in the subject methods is from 1:500 to 1:650,000, preferably from 1:1000 to 1:250,000, more preferably from 1:1200 to 1:200,000.

Water

The personal cleansing formulations of the subject invention typically contain water in an amount of from 20 to 90%, by weight more particularly from 50 to 85% by weight, based on the total weight of the formulation. Such water contents are representative of a relatively broad range of formulations, including both concentrated and non-concentrates products, with formulations having water contents of from 20 to less than 50% by weight of water being typical of concentrated products.

In use, the formulations are commonly diluted with water. The extent of dilution depends on the particular product form. Less commonly, but also contemplated for use herein are formulations that are foamed without dilution, typically through the use of pump dispensers in which product is passed through a screen in the pump.

In a preferred embodiment, the silver-containing compositions of the invention are used in combination with essential oil antimicrobial actives thymol and terpineol. Preferably, each is present in overall silver-containing composition at level of 0.01 to 2% of the composition.

Thymol is preferably present in 0.02 to 0.5%, more preferably up to 0.3% by weight, further more preferably up to 0.2% by weight of the composition. Thymol may be added to the antimicrobial composition in purified form. Alternatively, thyme oil or thyme extract comprising thymol may be added to the antimicrobial composition, while ensuring that thymol is present in the desired concentration in the composition of the present invention. Thyme oil or thyme extract is obtained from the thyme plant. Thyme plant refers to a plant belonging be genus *Thymus* and includes but is not limited to the following species: *Thymus vulgaris, Thymus zygis, Thymus satureoides, Thymus mastichina, Thymus broussonetti, Thymus maroccanus, Thymus pallidus, Thymus algeriensis, Thymus serpyllum, Thymus pulegoide,* and *Thymus citriodorus.*

The structures of thymol and its isomer carvacrol are given below:

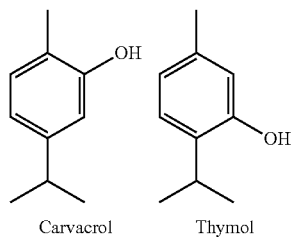

Carvacrol    Thymol

Terpineol is preferably present at 0.05 to 1% more preferably up to 0.5% by weight of the composition. The terpineol is preferably selected from alpha-terpineol, beta-terpineol, gamma-terpineol or mixtures thereof. It is particularly preferred that the terpineol is alpha-terpineol. Terpineol may be added to the antimicrobial composition in purified form. Alternatively pine oil comprising terpineol may be added to the antimicrobial composition.

The structure of a terpineol compound is given below:

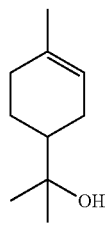

Optional Ingredients

If desired, the formulations may optionally include a detersive surfactant in addition to the fatty acid soap. Such detersive surfactants include, for example, anionic, zwitterionic and/or nonionic surfactants.

Examples of anionic surfactants suitable for use herein include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric mono- glyceride sodium sulfate, sodium lauryl sulfate, sodium laureth sulfate, potassium laureth sulfate, sodium lauryl sarcosinate, sodium lauroyl sarcosinate, potassium lauryl sulfate, sodium trideceth sulfate, sodium methyl lauroyl taurate, sodium lauroyl isethionate, sodium laureth sulfosuccinate, sodium lauroyl sulfosuccinate, sodium tridecyl benzene sulfonate, sodium dodecyl benzene sulfonate, sodium lauryl amphoacetate and mixtures thereof.

The anionic surfactant may be, for example, an aliphatic sulfonate, such as a primary $C_8$-$C_{22}$ alkane sulfonate, primary $C_8$-$C_{22}$ alkane disulfonate, $C_8$-$C_{22}$ alkene sulfonate, $C_8$-$C_{22}$ hydroxyalkane sulfonate or alkyl glyceryl ether sulfonate.

Zwitterionic surfactants suitable for use herein include, but are not limited to derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Illustrative zwitterionic surfactants are coco dimethyl carboxymethyl betaine, cocoamidopropyl betaine, cocobetaine, oleyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl betaine, and mixtures thereof. The sulfobetaines may include stearyl dimethyl sulfopropyl betaine, lauryl dimethyl sulfoethyl betaine, lauryl bis-(2-hydroxyethyl) sulfopropyl betaine and mixtures thereof.

Nonionic surfactants which may be used include the reaction products of compounds having a hydrophobic group and a reactive hydrogen atom. Exemplative are alcohols, acids, amides or alkyl phenols reacted with alkylene oxides, especially ethylene oxide either alone or with propylene oxide. Specific nonionics are $C_6$-$C_{22}$ alkyl phenols-ethylene oxide condensates, the condensation products of $C_8$-$C_{18}$ aliphatic primary or secondary linear or branched alcohols with ethylene oxide, and products made by condensation of ethylene oxide with the reaction products of propylene oxide and ethylenediamine. Other nonionics include long chain tertiary amine oxides, long chain tertiary phosphine oxides and dialkyl sulphoxides. Also useful are the alkyl polysaccharides.

When present the amount of additional detersive surfactant depends, in part, on the selection thereof, and the amount of the fatty acid soap. The subject personal cleansing formulations are soap-based, i.e., the total amount of fatty acid soap present therein exceeds the total amount of detersive surfactant that is not fatty acid soap. Commonly, the fatty acid soap comprises from 85 to 100 wt. %, more particularly from 90 to 100 wt. % of the total detersive surfactant present in the personal cleansing formulations.

The formulations typically include one or more skin benefit agents. The term "skin benefit agent" is defined as a substance which softens or improves the elasticity, appearance, and youthfulness of the skin (stratum corneum) by either increasing its water content, adding, or replacing lipids and other skin nutrients, or both, and keeps it soft by retarding the decrease of its water content. Included among the suitable skin benefit agents are emollients, including, for example, hydrophobic emollients, hydrophilic emollients, or blends thereof.

Useful skin benefit agents include the following: (a) silicone oils and modifications thereof such as linear and cyclic polydimethylsiloxanes; amino, alkyl, alkylaryl, and aryl silicone oils; (b) fats and oils including natural fats and oils such as jojoba, soybean, sunflower, rice bran, avocado, almond, olive, sesame, persic, castor, coconut, and mink oils; cacao fat; beef tallow and lard; hardened oils obtained by hydrogenating the aforementioned oils; and synthetic mono, di and triglycerides such as myristic acid glyceride and 2-ethylhexanoic acid glyceride; (c) waxes such as carnauba, spermaceti, beeswax, lanolin, and derivatives thereof; (d) hydrophobic and hydrophilic plant extracts; (e) hydrocarbons such as liquid paraffin, petrolatum, microcrystalline wax, ceresin, squalene, pristan and mineral oil; (f) higher fatty acids such as lauric, myristic, palmitic, stearic, behenic, oleic, linoleic, linolenic, lanolic, isostearic, arachidonic and poly unsaturated fatty acids (PUFA); (g) higher alcohols such as lauryl, cetyl, stearyl, oleyl, behenyl, cholesterol and 2-hexydecanol alcohol; (h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol monolaurate, glycerol distearate, glycerol tristearate, alkyl lactate, alkyl citrate and alkyl tartrate; (i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils; (j) polyhydric alcohols, for example, glycerine, sorbitol, propylene glycol, and the like; and polyols such as the polyethylene glycols, examples of which are: Polyox WSR-205 PEG 14M, Polyox WSR-N-60K PEG 45M, or Polyox WSR-N-750, and PEG 7M; (k) lipids such as cholesterol, ceramides, sucrose esters and pseudo-ceramides as described in European Patent Specification No. 556,957; (I) vitamins, minerals, and skin nutrients such as milk, vitamins A, E, and K; vitamin alkyl esters, including vitamin C alkyl esters; magnesium, calcium, copper, zinc and other metallic components; (m) sunscreens such as octyl methoxyl cinnamate (Parsol MCX) and butyl methoxy benzoylmethane (Parsol 1789); (n) phospholipids; and (o) anti-aging compounds such as alpha-hydroxy acids and beta-hydroxy acids. Skin benefit agents commonly account for up to 30 wt. % of the liquid soap formulation, with levels of from 0 to 25 wt. %, more particularly from 0 to 20 wt %, being typical of the levels at which those skin benefit agents generally known as "emollients" are employed in many of the subject formulations. Preferred skin benefit agents include fatty acids, hydrocarbons, polyhydric alcohols, polyols and mixtures thereof, with emollients that include at least one $C_{12}$ to $C_{18}$ fatty acid, petrolatum, glycerol, sorbitol and/or propylene glycol being of particular interest in one or more embodiments.

Other optional ingredients include water soluble/dispersible polymers. These polymers can be cationic, anionic, amphoteric or nonionic types with molecular weights higher than 100,000 Dalton. They are known to increase the viscosity and stability of liquid personal cleansing formulation, to enhance in-use and after-use skin sensory properties, and to enhance lather creaminess and lather stability. When present, the total amount of such polymers commonly ranges from 0.1 to 10% by weight of the personal cleansing formulation.

Examples of water soluble or dispersible polymers include the carbohydrate gums such as cellulose gum, microcrystalline cellulose, cellulose gel, hydroxyethyl cellulose, hydroxypropyl cellulose, sodium carboxymethylcellulose, methyl cellulose, ethyl cellulose, guar gum, gum karaya, gum tragacanth, gum arabic, gum acacia, gum agar, xanthan gum and mixtures thereof; modified and nonmodified starch granules and pregelatinized cold water soluble starch; emulsion polymers such as Aculyn® 28, Aculyn® 22 or Carbopol® Aqua SF1; cationic polymer such as modified polysaccharides including cationic guar available from Rhone Poulenc under the trade name Jaguar C13S, Jaguar C14S, Jaguar C17, or Jaguar C16; cationic modified cellulose such as UCARE Polymer JR 30 or JR 40 from Amerchol; N-Hance® 3000, N-Hance® 3196, N-Hance® GPX 215 or N-Hance® GPX 196 from Hercules; synthetic cationic polymer such as Merquat® 100, Merquat® 280, Merquat® 281 and Merquat® 550 sold by Nalco; cationic starches such as StaLok® 100, 200, 300 and 400 sold by Staley Inc.; cationic galactomannans such as Galactasol® 800 series by Henkel, Inc.; Quadrosoft® LM-200; and Polyquaternium-24. Also suitable are high molecular weight polyethylene glycols such as Polyox® WSR-205 (PEG 14M), Polyox® WSR-N-60K (PEG 45), and Polyox® WSR-301 (PEG 90M).

Preservatives/antimicrobials can desirably be incorporated into the personal cleansing formulations of this invention to protect against the growth of potentially harmful microorganisms. Suitable traditional preservatives for formulations of this invention are alkyl esters of para-hydroxybenzoic acid. Other preservatives/antimicrobials which have more recently come into use include hydantoin derivatives, propionate salts, and a variety of quaternary ammonium compounds. Among the preservatives/antimicrobials of particular interest are phenoxyethanol, methyl paraben, propyl paraben, imidazolidinyl urea, sodium dehydroacetate and benzyl alcohol. Other preservatives of particular interest are dimethyloldimethylhydantoin (Glydant XL1000), parabens, sorbic acid, thymol and terpineol to name a few (with combinations of thymol and terpineol as described, for example, in U.S. Patent Application Publication No. 2011/0223114 incorporated herein by reference, being of particular interest in one or more embodiments).

The preservatives/antimicrobials should be selected having regard for the use of the formulation and possible incompatibilities between the preservatives and other ingredients. Preservatives are preferably employed in amounts ranging from 0.01 to 2% by weight of the personal cleansing formulation.

Additional optional ingredients which may be present in the subject personal cleansing formulations are, for example: fragrances; sequestering and chelating agents such as tetrasodium ethylenediaminetetraacetate (EDTA), ethane hydroxyl diphosphonate (EHDP), and etidronic acid, aka 1-hydroxyethylidene diphosphonic acid (HEDP); coloring agents; opacifiers and pearlizers such as zinc stearate, magnesium stearate, $TiO_2$, ethylene glycol monostearate (EGMS), ethylene glycol distearate (EGDS) or Lytron 621 (Styrene/Acrylate copolymer) and the like; pH adjusters; antioxidants, for example, butylated hydroxytoluene (BHT) and the like; stabilizers; suds boosters, such as for example, coconut acyl mono- or diethanol amides; ionizing salts, such as, for example, sodium chloride and sodium sulfate, and other ingredients such as are conventionally used in liquid soap formulations. The total amount of such additional optional ingredients is typically from 0 to 10% by weight, more particularly from 0.1 to 5% by weight, based on the total weight of the personal cleansing formulation.

The personal cleansing formulations of this invention are of interest with respect to biocidal activity against Gram positive bacteria, including in particular S. aureus. Other Gram, positive bacteria against which the soap formulations are of interest are S. epidermidis, and/or Corynebacteria, in particular, Corynebacteria strains responsible for the hydrolysis of axilla secretions to malodorous compounds. Desirably, the formulations provides a $\log_{10}$ reduction in biocidal activity against Staphylococcus aureus ATCC 6538 of at least 2.5, preferably of least 3, at a contact time of 30 seconds and even more preferably provides a $\mathrm{Log}_{10}$ Reduction against S. aureus ATCC 6538 of at least 1.5 even more preferably at least 2 at a contact time of 10 seconds.

In use, the personal cleansing formulations are diluted, as needed, to form aqueous cleansing compositions that are applied to the skin for contact times less than 1 minute, more particularly 30 seconds or less (with contact times of 10 to 30 seconds being of interest with respect to contact times of a moderate to a relatively long duration and contact times of 10 seconds or less being of interest with respect to contact times of short to moderate duration) and thereafter is removed from the skin, typically by rinsing with water. The personal cleansing formulation can be diluted before, after or simultaneous with its being placed on the skin, with dilution typically occurring by the formulation being worked into a lather in the hands or on an applicator, such as a facecloth, sponge or pouf.

Manufacture

The personal cleansing formulations herein described may be produced by preparative techniques as are conventional in the art. In one very general methodology, to a heated aqueous phase of water, is added melted fatty acid, followed by caustic (to neutralize the fatty acid and form soap), synthetic detergents and co-solvents; the remaining ingredients are added, as appropriate, as the product is cooled to room temperature.

The personal cleansing formulations may be provided in a variety of different product forms including, for example, hand, face and body washes, shower gels, and the like. The formulations may be provided in bottles, pump dispensers, tubes, sachets, or other packaging suitable for the product form.

EXAMPLES

The following non-limiting examples are provided to further illustrate the invention; the invention is not in any way limited thereto. The following protocol was used to evaluate biocidal activity.

In-Vitro Time-Kill Protocol

Soap Solution Preparation

Solution preparation depends, in part, on the particular form of the liquid soap formulation. For example, formulations that are not diluted in use, e.g., self-foaming formulations, are employed as is. A formulation that contains 30 wt. % or less of detersive surfactant and which is intended to be diluted in use is mixed with an equal amount, by weight, of water to form a soap solution containing 50 wt % of the initial formulation. A formulation that contains more than 30 wt % of detersive surfactant and which is intended to be diluted in use is mixed with water to form a soap solution containing 16 wt % of the initial formulation.

Bacteria

Staphylococcus aureus ATCC 6538, were used in this study to represent Gram positive bacteria, respectively. The bacteria was stored at −80° C. Fresh isolates were cultured twice on Tryptic Soy Agar plates for 24 hours at 37° C. before each experiment.

In-Vitro Time-Kill Assay

Time-kill assays are performed according to the European Standard, EN 1040:2005 entitled "Chemical Disinfectants and Antiseptics—Quantitative Suspension Test for the Evaluation of Basic Bactericidal Activity of Chemical Disinfectants and Antiseptics—Test Method and Requirements (Phase 1)" incorporated herein by reference Following this procedure Growth-phase bacterial cultures at $1.5 \times 10^8$ to $5 \times 10^8$ colony forming units per ml (cfu/ml) are treated with the soap solutions (prepared as described above) at 25° C. In forming the test sample 8 parts by weight of the soap solution, prepared as described above, is combined with 1 part by weight of culture and 1 part by weight of water. After 10, 30, and 60 seconds of exposure, samples are neutralized to arrest the antibacterial activity of the soap solutions. Then test solutions are serially diluted, plated on solid medium, incubated for 24 hours and surviving cells are enumerated. Bactericidal activity is defined as the log reduction in cfu/ml relative to the bacterial concentration at 0 seconds. Cultures not exposed to any soap solutions serve as no-treatment controls.

The $\log_{10}$ reduction was calculated using the formula:

$$\mathrm{Log}_{10} \text{ Reduction} = \log_{10} \text{ (numbers control)} - \log_{10} \text{ (test sample survivors)}$$

Examples 1 to 3

Liquid soap formulations were prepared as indicated in Table 2 below.

TABLE 2

| Ingredient (wt. %) | Liquid Soap 1 | Liquid Soap 2 | Liquid Soap 3 |
| --- | --- | --- | --- |
| Water | Balance to 100 | Balance To 100 | Balance To 100 |
| Cellulose Ether (Methocel ™ 40-100 from Dow Chemical) | 0.30 | 0.30 | 0.30 |
| BHT | 0.05 | 0.05 | 0.05 |
| EDTA | 0.13 | 0.13 | 0.13 |
| EHDP | 0.08 | 0.08 | 0.08 |
| Glycerine | 0.50 | 0.50 | 0.50 |
| Laurie Acid Soap | 5.8 | 5.8 | 5.8 |
| Myristic Acid Soap | 6.7 | 6.7 | 6.7 |
| Palmitic Acid Soap | 2.1 | 2.1 | 2.1 |
| KOH | 3.60 | 3.60 | 3.60 |
| Sodium laureth ether Sulfate-1EO (SLES) | 2.10 | 2.10 | 2.10 |
| Cocamidopropyl Betaine | 0.75 | 0.75 | 0.75 |
| Methylchloroisothiozolinone (Kathon ™ CG) | 0.10 | 0.10 | 0.10 |
| Silver Sulfate | — | 0.0001 | 0.0005 |

The biocidal activity of the liquid soaps formulations was evaluated following the above described In-Vitro Time-Kill Protocol. Biocidal activity results are reported in Table 3.

TABLE 3

| Biocidal Activity Log$_{10}$ Reduction against *S. aureus* ATCC 6538 | | | |
|---|---|---|---|
| | Contact Time | | |
| | 10 Seconds | 30 Seconds | 60 Seconds |
| Liquid Soap 1 (Comp.) | 1.0 | 2.0 | 2.9 |
| Liquid Soap 2 | 1.5 | 2.8 | 4.3 |
| Liquid Soap 3 | 2.5 | 3.4 | 4.1 |

As demonstrated by the Table 3 data, at the indicated contact times, liquid soap 2 and liquid soap 3 had greater bactericidal efficacy against *S. aureus* ATCC 6538 than liquid soap 1 (no silver component).

The invention claimed is:

1. A method of reducing Gram positive bacteria comprising *Staphylococcus aureus*, on human skin which comprises:
   a) providing a liquid cleansing formulation comprising:
      (i) from 5 to 65% by weight, based on the total weight of the formulation, of fatty acid soaps, wherein the fatty acid soaps are derived from fatty acids comprising lauric acid and oleic acid,
      (ii) 0.1 to 100 ppm by weight, based on the total weight of the formulation, of at least one silver(I) compound having a silver ion solubility (in water at 25° C.) of at least $1\times10^{-4}$ mol/L; and
      (iii) 20 to 90% by weight water;
   b) diluting the liquid cleansing formulation to form an aqueous soap composition having a pH in the range of 9 to 11, said aqueous soap composition comprising:
      (i) from 0.2 to 25% by weight of the fatty acid soaps;
      (ii) said at least one silver(I) compound having a silver ion solubility (in water at 25° C.) of at least $1\times10^{-4}$ mol/L;
   c) reducing the *Staphylococcus aureus* present on human skin by applying to the human skin said aqueous soap composition;
   d) allowing the aqueous soap composition to remain on the human skin for a contact period of under 1 minute; and
   d) rinsing the aqueous soap composition from the human skin.

2. A method as described in claim 1 wherein the silver(I) compound is present in the liquid cleansing formulation in an amount of from 1 to 50 ppm, based on the total weight of the formulation.

3. A method as described in claim 1 wherein the silver compound comprises silver oxide.

* * * * *